United States Patent [19]

Pawliszyn

[11] Patent Number: 5,395,502
[45] Date of Patent: Mar. 7, 1995

[54] APPARATUS FOR PERFORMING AND UNIVERSALLY DETECTING CAPILLARY ISOELECTRIC FOCUSING WITHOUT MOBILIZATION USING CONCENTRATION GRADIENT IMAGING SYSTEMS

[75] Inventor: Janusz B. Pawliszyn, Waterloo, Canada

[73] Assignee: Anthony R. Torres, Centerville, Utah

[21] Appl. No.: 201,670

[22] Filed: Feb. 25, 1994

Related U.S. Application Data

[63] Continuation of Ser. No. 819,325, Jan. 13, 1992, abandoned, which is a continuation-in-part of Ser. No. 657,066, Feb. 19, 1991, Pat. No. 5,153,666, which is a continuation-in-part of Ser. No. 271,008, Nov. 14, 1988, Pat. No. 4,993,832.

[51] Int. Cl.$^6$ .................... G01N 27/26; G01N 27/447
[52] U.S. Cl. ............... 204/299 R; 204/182.9; 204/183.2
[58] Field of Search ............. 204/183.2, 182.9, 299 R; 356/344

[56] References Cited

U.S. PATENT DOCUMENTS

| | | | |
|---|---|---|---|
| 3,623,812 | 11/1971 | Hennig | 356/344 |
| 3,745,484 | 7/1973 | Caristi | 356/246 |
| 4,547,071 | 10/1985 | Teitelbaum | 356/344 |
| 4,591,550 | 5/1986 | Hafeman et al. | 435/4 |
| 4,784,494 | 11/1988 | Pawliszyn | 356/432 |
| 4,927,265 | 5/1990 | Brownlee | 356/73 |
| 4,940,333 | 7/1990 | Pawliszyn | 356/432 |
| 4,993,832 | 2/1991 | Pawliszyn | 356/128 |
| 5,021,646 | 6/1991 | Weinberger et al. | 356/319 |
| 5,153,666 | 10/1992 | Pawliszyn | 356/128 |
| 5,235,409 | 8/1993 | Burgi et al. | 356/436 |

FOREIGN PATENT DOCUMENTS 1098307 1/1968 United Kingdom .

OTHER PUBLICATIONS

Jiaqi Wu and Janusz Pawliszyn "High-Performance Capillary Isoelectric Focusing with a Concentration Gradient Detector" Analytical Chemistry vol. 64, No. 2 (Jan. 15, 1992).

Jiaqi Wu and Janusz Pawliszyn "Universal Detection for Capillary Isoelectric Focusing without Mobilization Using a Concentration Gradient Imaging System'-'πAnalytical Chemistry, vol. 64, No. 2 (Jan. 15, 1992).

Primary Examiner—John Niebling
Assistant Examiner—John S. Starsiak, Sr.
Attorney, Agent, or Firm—Mallinckrodt & Mallinckrodt

[57] ABSTRACT

The separations resulting from capillary electrophoresis performed in a microbore capillary tube are detected on-line by focusing a light beam in the form of a line or sheet of light on the capillary passage in which the separations take place so that the width of the sheet of light encompasses the length of the passage in which separations of interest are expected to take place. The separations form concentration gradients in the capillary passage encompassed by the light beam and cause refraction of portions of the light beam. The variation in the intensity of light along the width of the light beam after passage through the sample is sensed and is indicative of the concentration gradients and separation occurring in the sample. An apparatus including a relatively short capillary tube with liquid reservoirs secured at each end may be used with the detector to perform various capillary electrophoretic separation techniques. By using a reagent which reacts with an analyte not having an isoelectric point to form a product having an isoelectric point, such analyte may be detected and measured by isoelectric focusing techniques.

15 Claims, 10 Drawing Sheets

APPARATUS FOR PERFORMING AND UNIVERSALLY DETECTING CAPILLARY ISOELECTRIC FOCUSING WITHOUT MOBILIZATION USING CONCENTRATION GRADIENT IMAGING SYSTEMS

RELATED APPLICATIONS

This is a continuation of application Ser. No. 07/819,325, filed Jan. 13, 1992, now abandoned, which is a continuation-in-part of application Ser. No. 07/657,066, filed Feb. 19, 1991, entitled "Method and Apparatus for Detecting Concentration Gradients", now U.S. Pat. No. 5,153,666, which was a continuation-in-part of application Ser. No. 07/271,088, filed Nov. 14, 1988, also entitled "Method and Apparatus for Detecting Concentration Gradients", now U.S. Pat. No. 4,993,832.

BACKGROUND OF THE INVENTION

1. Field

The invention is in the field of capillary electrophoresis, detection methods for capillary electrophoresis and apparatus based on such methods, and on Schlieren optics.

2. State of the Art

It has been known for some time that a refractive index gradient such as produced by a concentration gradient in a fluid such as a gas, liquid, or supercritical fluid, will cause deflection of light passed through the gradient. The optical method of observing and measuring the deflection of light caused by refractive index gradient fields is generally referred to as Schlieren optics. In the past, Schlieren images resulting from light deflections have been recorded on photographic plates and the plates then analyzed for light intensity distribution using densitometers. Recently, evaluation of the photographic images has been done by computer. These methods are useful in studying plasmas where very complicated toroidal and parabolic shapes are generated.

U.S. Pat. No. 4,547,071 discloses a sensor for measuring density gradients in a nonhomogeneous fluid sample using Schlieren optics. In such sensor, a laser light beam is directed through a sample chamber and is moved along said chamber. A quadrant light position sensor located on the opposite side of the chamber detects the deflection of the laser light beam as it is moved through the sample. The amount of deflection indicates the density gradient at any point in the sample. Rather than moving the laser beam along the sample chamber, the beam can be held constant and the sample chamber with sample therein moved. However, moving a laser and detector together in relation to a sample chamber and keeping the laser beam focused on the sample chamber, even a relatively large chamber, is difficult, as is moving a sample chamber through the laser beam so as to keep the laser beam properly focused. Trying to do either with a small capillary sample chamber is very difficult and impractical.

My U.S. Pat. Nos. 4,784,494, 4,940,333 and 4,993,832 show detectors that can be used to detect concentration and thermal gradients in very small samples. The detectors utilize a light source to generate one or two probe beams of light that pass through the sample having the gradient to be detected and the deflection of the probe beam or beams is measured on a beam position detector. Various light sources may be used to generate the probe beam or beams, such as a laser or light emitting diode (LED). These detectors, however, are designed generally to be used where the gradients to be detected move through the probe beam or beams of light.

Capillary electrophoresis has become an important separation method in bioanalytical chemistry. Separation and detection of very small amounts of biological samples, about pL-nL volumes, can be achieved with capillary electrophoresis. This is generally not possible with more conventional methods of separation, even with high performance liquid chromatography. There are several capillary electrophoresis separation methods in use for different kinds of samples. They include capillary zone electrophoresis, moving boundary capillary electrophoresis, capillary isotachophoresis, and capillary isoelectric focusing. Capillary zone electrophoresis, moving boundary capillary electrophoresis, and isotachophoresis all have the advantage that the sample moves through a capillary sample separation chamber during the separation so can be used with the detectors of my cited prior patents. Capillary zone electrophoresis and moving boundary capillary electrophoresis are dynamic processes where separation occurs at an instant in time and then the zones immediately begin to diffuse and disperse. The diffusion takes place as the samples move through the sample chamber to the detector. This makes detection of the various zones more difficult and less accurate than may be desired. Isotachophoresis has the advantage that the zones stay relatively sharp as the sample moves through the capillary, but isotachophoresis is a difficult process to work with.

Isoelectric focusing has been employed for separation of sample components based on differences in their isoelectric points. Recently, the development of capillary electrophoresis techniques has generated interest in preforming the isoelectric focusing in capillaries, since efficient dissipation of Joule heat from a 10-100 $\mu$m diameter capillary eliminates convection effects which occur in larger sample chambers and enables highly efficient separations. Capillaries with microbores, i.e., with very small inner diameter, also require only small amounts of sample, which is desirable for analysis of biological materials, such as monoclinal antibodies and other proteins. The capillary isoelectric focusing process involves establishing an electrical field between the ends of the capillary and establishing a stable pH gradient inside the capillary using a mixture of amopholytes. At the same time, an ampholytic analyte, such as a protein, moves along this pH gradient and is focused at the point where the pH is equivalent to its isoelectric point. The migration then ceases. Thus, a stationary condition is reached and maintained in the capillary. During this separation process, narrow Gaussian bands are generated with high peak concentrations which results in high separation resolution of the analytes. In order to detect the now focused analytes with available detectors, the focused zones must be moved through a stationary detector which is usually located at one end of the capillary. Thus, the focusing of the sample in the capillary is followed by a mobilization process. The commonly used mobilization process requires addition of salt to the electrolyte at one end of the capillary. The salt causes changes in pH at that end of the capillary. Because of this pH shift, the analytes focused in the capillary are no longer at their isoelectric points and will consequently move or migrate toward the end of the capillary and will pass through the detector. During the mobilization process, distortion of the focused zones and loss in resolution are unavoidable. Further, the mobilization process also takes at least about 15 minutes compared to the about five minutes required for the focusing itself using commonly available isoelectric focusing systems. Since the detection is necessary, the required mobilization makes the isoelectric focusing a relatively slow separation method thought to have little advantage compared to other capillary electrophoretic techniques. Therefore, it is necessary to develop an on-line detection method to eliminate the mobilization step and thereby improve the speed and performance of detection using the isoelectric focusing separation technique.

Several on-line scanning spectroscopic and radiometric detection methods have been developed for electrophoresis performed on slabs. However, such methods cannot be satisfactorily used with electrophoresis carried out in microbore capillaries because of their small size. Recently, there have been attempts made to continuously monitor capillary isoelectric focusing separation. In one instance, photographs were taken of the focusing of blue dye stained proteins inside a 0.4–0.6 mm i.d. capillary, and the photographs used to study the zones of proteins. However, this technique requires labeling of the proteins and can not give good quantitative information. In another instance, the separation in the capillary was monitored using chemical electrodes spaced along the length of the sample chamber. Although a complicated 100 chemical electrode array was used, the resolution obtained in these experiments was very poor.

With currently available capillary electrophoresis equipment, the capillary tube is generally about a meter in length and each end must be manually positioned in a container holding solute or sample to be separated. The longer the capillary tube, the longer the time necessary for a sample to move through the tube. When a new sample is to be separated, one end of the capillary tube has to be moved to another container which contains the new sample. Also, as the ends of the capillary are moved from container to container, the electrodes necessary for operation of the system must also be moved. Since voltages up to about 10 KV are required to operate the system, the person moving the capillary tube and electrodes from container to container may easily come into dangerous contact with the electrodes.

One of the most promising applications for capillary electrophoresis is for routine analysis in research laboratories, pharmaceutical manufacturing facilities, and hospitals. However, in many cases, relatively rapid separation and accurate detection of samples is required, because the feedback of the analyzed data is essential for observing effectiveness of a therapy, adjusting drug doses in treatment of patients in hospitals, or controlling process conditions in industrial manufacturing. Also, since different methods of capillary electrophoresis apply to different types of samples and situations, it would be convenient to be able to run different methods on the same instrument. It is impossible for current commercial capillary electrophoresis instruments to change from one separation method to another. Each instrument and capillary cartridge is designed for a particular type of separation, e.g., for capillary isotachophoresis, or for moving boundary capillary electrophoresis. A further problem is that current commercially available capillary electrophoresis instruments lack sensitive, universal, and inexpensive detectors.

Although conventional absorption spectrophotometric detectors can be universal, they are not sensitive enough for capillary electrophoresis using narrow capillaries, and an expensive monochromator is required. The fluorometric detectors in use not only need expensive lasers and photomultipliers but also require fluorescent derivatization for most analytes. The commercial capillary electrophoresis instruments with such detectors are usually expensive and large devices.

Also, it is sometimes desirable to separate and identify sample components or determine if such components are present in a sample, for components which do not lend themselves to separation by electrophoretic techniques. Thus, other more complicated detectors and detection methods are required to detect these components.

SUMMARY OF THE INVENTION

According to the invention, it has been found that concentration gradient detection is uniquely suited for use as a detection means and method for detecting the various bands of components as separated by capillary isoelectric focusing techniques. It has also been found that isoelectric focusing can be effectively accomplished in relatively short capillary tubes, such as capillary tubes with about ten centimeters overall length, and that the actual separations take place within an even shorter portion of such tubes. Further, it has been found that a light beam can be generated as a sheet or line of light, i.e., a beam of predetermined width with very small height dimension, that can be focused on the capillary passage in the capillary tube and the separated sample therein so as to extend along the capillary passage through the portion containing the separated sample. The light within the light beam is deflected by the concentration gradients in the sample along the width of the light beam to produce variations in the intensity of the light beam along its width which are representative of the concentration gradients established in the capillary passage by the isoelectric focusing. By monitoring the light beam after passing through the capillary tube and sample therein, the separation of the sample can be easily and quickly determined.

In a preferred embodiment of the invention, the intensity of the light beam after passing through the sample is monitored by a light detector in the form of a photodiode array extending along the portion of the capillary tube where the expected separations take place. The photodiode array is made up of individual sensing elements of a size small enough to be able to resolve and detect the differences in light intensity caused by the refraction of the light passing through the concentration gradients in the sample. With such an arrangement, the light source, detector, and sample chamber, i.e., capillary passage, are all fixed relative to one another to maintain accurate light beam focusing and detection, yet the measurements can be made with a stationary sample separation in the capillary. It is not necessary to move the sample through the light beam to obtain a measurement. The entire sample of interest is comprehended by the light beam passing through the sample. Further, in the preferred embodiment, the light beam is generated by an inexpensive He-Ne laser with a cylindrical lens to convert the beam from the laser into a sheet of light and to focus the sheet onto the capillary passage. Various other means of producing the sheet of light could be used, however.

In an alternate preferred embodiment of the invention, the intensity of the light beam after passing through the sample is monitored by a light detector in the form of a single photodiode having a narrow sensing area compared to the width of the light beam to be detected so that the detector senses only a small portion of the beam at any one time. The photodiode is mounted for movement along the sample chamber where the expected separations take place. By moving the photodiode along the sample chamber through the beam, the diode measures the light intensity at the particular location it moves through and thereby provides an output proportional to the intensity of the beam at each point the photodiode moves through. Since the light beam is not moved with the detector, i.e., the sample chamber and the light beam remain fixed in relation to one another, the problem with maintaining alignment of the light beam and sample chamber is not present.

A simple and easy to use capillary electrophoresis apparatus can be constructed with a first reservoir and a second reservoir connected and held together with a sheet of glass, such as a microscope slide. A capillary tube secured to the slide extends between the reservoirs so that the capillary passage through the capillary tube extends between and connects the two reservoirs. Electrodes are inserted into the reservoirs and the reservoirs are configured to easily accept a tube extending from a syringe to enable liquid to be easily added to or withdrawn from a reservoir. Thus, the solute or sample can be easily changed in a reservoir by withdrawing it from the reservoir with the syringe and adding new solute or sample, or mixture, with a syringe. In such apparatus, the capillary passage will usually be about ten centimeters long and have a capillary diameter of between ten and one-hundred microns. The reservoirs have small capacity so that only small sample volumes are needed. The volume of the reservoir, however, will be larger than the volume of the capillary so that enough sample will be present to fill the capillary. With such an arrangement, any method of electrophoresis may be used. It is not necessary to use a different apparatus for each different method of electrophoresis.

A method of the invention allows electrophoretic separation, particularly using the isoelectric focusing technique, for various sample components not otherwise subject to such separation. The method involves selecting a reagent capable of separation and having a high degree of specificity for the component to be detected. The reagent is added to the sample, preferably in an amount sufficient to interact with all of the sample component to be detected that might be in the sample. The reagent has its own isoelectric point and the product of reagent and component has a different isoelectric point. Thus, with isoelectric focusing, the reagent in the sample, and the product of reagent and component in the sample, will each be separated to form different bands in the sample which can be detected by the detector of the invention.

THE DRAWINGS

The best mode presently contemplated for carrying out the invention is shown in the accompanying drawings in which:

FIG. 1 is schematic representation of a light beam passing through a gradient;

FIG. 2, a schematic representation of a light beam passing through a sample chamber, showing the deflection angle produced by the presence of a refractive index gradient in the chamber;

FIG. 3, a second schematic representation of a light beam passing through a sample chamber with a concentration gradient;

FIG. 4, a schematic representation of a light beam passing through a sample chamber similar to FIG. 2, but showing a wide beam with a gradient in part of the beam;

FIG. 5, a further schematic representation of a wide light beam passing through a sample chamber with a concentration gradient in a portion of the beam;

FIG. 6, a vertical section through the capillary passage of an electrophroesis apparatus of the invention;

FIG. 7, a fragmentary horizontal section taken on the line 7—7 of FIG. 6, but showing the light source, lenses, and detector in top plan view;

FIG. 8, a fragmentary vertical section taken through a capillary tube showing sample component separation resulting from isoelectric focusing;

FIG. 9, a vertical section through a light beam formed by the apparatus of the invention;

FIG. 10, a fragmentary vertical section taken on the line 10—10 of FIG. 7;

FIG. 11, a fragmentary top plan view of an alternate detector of the invention;

FIG. 12, a block diagram of a detector of the invention;

FIG. 13, a curve representing the light intensity profile of a probe light beam passing through a sample separated by isoelectric focusing in the apparatus of the invention and produced as the output signal by a moving detector;

FIG. 14, a set of three curves labeled a, b, and c with curve a representing a peak of the curve of FIG. 13, curve b representing the integral of curve a, and curve c representing the integral of curve b and second integral of curve a;

FIG. 15, a set of three curves labeled a, b, and c representing the light intensity profiles of a probe light beam passing through a sample during separation by isoelectric focusing in the apparatus of the invention and produced as the output signals by a moving detector;

FIG. 16, a set of three curves labeled a, b, and c representing the light intensity profiles of a probe light beam passing through a sample during separation by isoelectric focusing in the apparatus of the invention and produced as the output signal by a diode array detector;

FIG. 17, a fragmentary vertical section of an alternate sample receiving reservoir usable with the apparatus of FIGS. 6 and 7;

FIG. 18, a set of three curves labeled a, b, and c being schematic representations of light intensity profiles showing separations obtained through a method of the invention;

FIG. 19, a curve representing the concentration profile of a sample separated in the apparatus of the invention and mobilized to move through a detector and produced as the output signal by the detector;

FIG. 20, a set of two curves labeled a and b showing the concentration gradient profiles of the same sample separated using capillary zone electrophoresis and moving boundary capillary electrophoresis; and FIG. 21, a curve showing the concentration gradient profile for the same sample as used for FIG. 20, showing the sample separated by isoelectric focusing.

DETAILED DESCRIPTION OF THE PREFERRED EMBODIMENT

Figure 1:
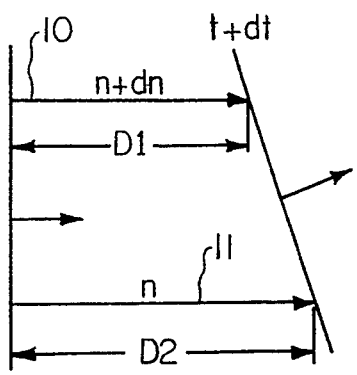

It is well known that light passing through a refractive index gradient in a solution is deflected. The physical reason for light deflection when passing through this gradient lies in the relationship between the refractive index and light propagation velocity. Different parts of the light advance to a different degree with time, which generates the phase shift. Thus, as shown in FIG. 1, during a given time period t+dt, light at the top of a light beam indicated by arrow 10 which is passing through a solution with a refractive index of n+dn will travel a distance of D1. The light at the bottom of the light beam indicated by arrow 11 which is passing through a solution with a refractive index of n will travel a distance D2. This results in a tilt of the light wavefront and since light travels perpendicular to the wavefront, the light beam is tilted as illustrated. In FIG. 1, D2 is greater than D1 resulting in an upward tilt, but depending upon the values of n and n+dn, the tilt could be downward.

The light path through the refractive index gradient can be calculated by using the Fermat principle that the light path through the medium is such that the time necessary for its traversal is minimum. The relationship between the angle of deflection, $\theta$, and the refractive index gradient normal to the light propagation dn/dx and path length through this gradient, D, can be written as $$\tan\theta = \sin h$$
$$(D/n)(dn/dx) = (D/n)(dn/dx) + (dn/dx)^3(D^3/n^3 3!) + (dn/dx)^5(D^5/n^5 5!) + \ldots$$

where n is the refractive index of the medium. In situations where the sensor of the invention will be used, D and $\theta$ are small. We can then approximate:

$$\theta = (D/n)(dn/dx)$$

Figure 2:
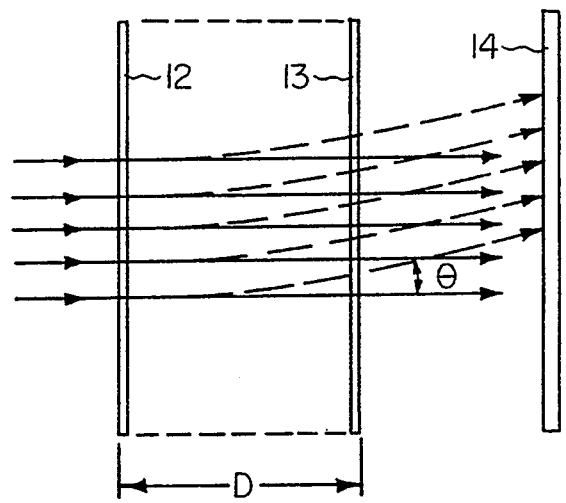

FIG. 2 illustrates the detection principle behind this method. With a nonuniform distribution of a solute in the sample chamber shown schematically between sample chamber walls 12 and 13 giving a sample chamber distance D, a concentration gradient is established. This gradient forms the corresponding refractive index gradient dn/dx=(dn/dc)(dc/dx), which then tilts or deflects the propagating light beam by angle $\theta=(D/n)(dn/dc)(dc/dx)$. This deflection can be measured by measuring the position of the light beam on the position detector 14. The information produced during the measurement of the concentration gradient relates to the universal property of the solute—refractive index n. Consequently, the concentration gradient produced by any solute that has a different n than the solvent will be detected by noting a deflection or tilt in the light beam.

Figure 3:
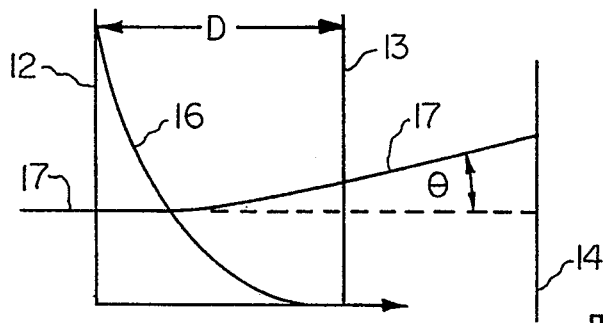

FIG. 3 shows the same principal as FIG. 2, but illustrates it somewhat differently. Thus, if a concentration gradient represented by line 16 exists in a sample in a sample chamber defined by walls 12 and 13, a probe beam of light 17 directed through the sample will be deflected as indicated above by an angle $\theta$. This causes the position of the beam to move on the surface of the position sensor 14 as indicated above.

Figure 4:
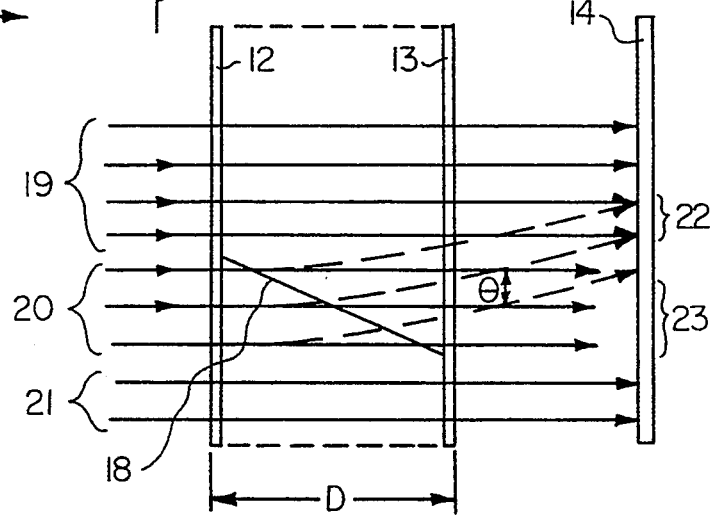

FIG. 4 is similar to FIG. 2, but shows a wide light beam with a concentration gradient 18 within the width of the light beam. Thus, rather than the light beam being uniformly deflected as shown in FIGS. 1, 2, and 3, a portion of the light beam 19, on one side of the gradient 18, which does not pass through a gradient, passes straight through the sample to detector 14. Portion 20 of the light beam passes through the gradient 18 and is deflected by angle $\theta$ as shown by the broken arrows, and falls onto detector 14 partially overlapping portion 19. Where the overlap occurs on the detector, indicated at 22, the light striking detector 14 is brighter than in non overlapping areas. Portion 21 of the light beam on the other side of the gradient 18, again passes straight through the sample and onto detector 14. As indicated in FIG. 4, there will be an area 23 where little or no light will fall. Thus, the single light beam after passing through a sample with one or more gradients therein will have varying intensity indicating the gradients present in the sample. A gradient in the sample will generally result in a bright spot followed by a spot of very little intensity, or, if just measuring intensity, a level representing the light passing straight through the sample, an increased or positive signal (the increased intensity), followed by decreased or negative signal (the decreased intensity), followed again by the level representing the light passing straight through the sample.

If the detector 14 is broken down into many small detectors, such as an array of detectors, each detector detecting the light from a small portion of the beam, a comparison or scanning of the individual detectors will produce an output signal representative of the intensity of the light beam falling on the array along its length. Alternatively, a single, small detector which detects only a portion of the light beam could be positioned to be moved through the beam along its width and measure the light intensity as it is moved.

Figure 5:
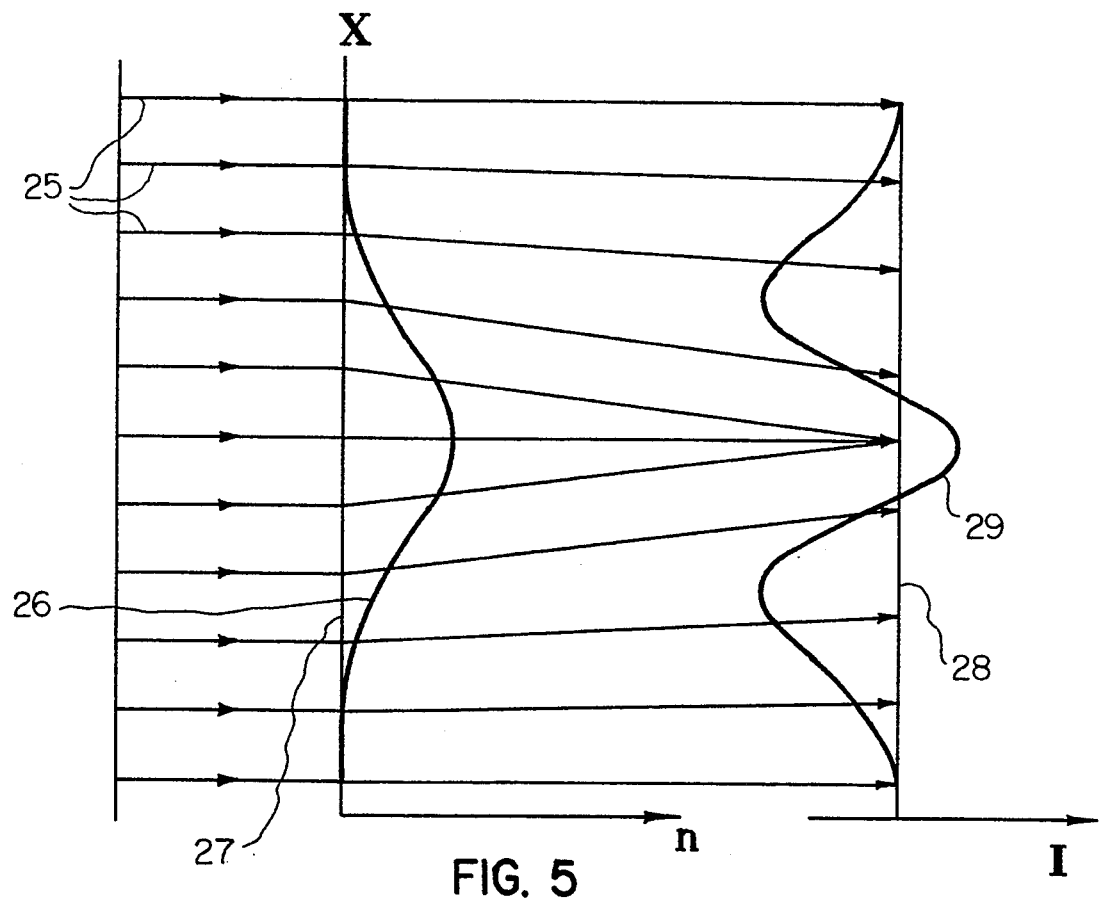

FIG. 5 shows the same principal as FIG. 4, but relates it more directly to a system of the invention. Thus, again, the light beam may be considered as many parallel light rays 25. A gaussian refractive index gradient produced by a similar gaussian concentration gradient as would appear in a sample in a sample chamber is represented schematically by curve 26. Line 27 represents both the plane of the sample chamber where the light beam passes through the sample and an axis indicating length along the sample chamber for the refractive index gradient curve 26. Axis n represents the refractive index of the sample within the sample chamber. Line 28 represents the detector plane and also an axis representing the intensity of light passing straight through the sample chamber when no refractive index gradient is present. Curve 29 represents the intensity I of the light striking the detector plane. When the light beam passes through the sample chamber, the individual light rays 25 are refracted and bent out of their original path upon encountering the refractive index gradient 26 produced by a concentration gradient inside the sample chamber. If the intensity of each light ray is constant, equalling $I_o$, the relative changes of the light intensity on the detector plane can be given by:

$$\frac{\Delta I(x)}{I_0} = L\int_0^d \frac{\partial^2}{\partial x^2}[\log n(x)]dz = Ld\left\{\frac{1}{n(x)}\frac{d^2n}{dx^2} - \left[\frac{1}{n(x)}\frac{dn}{dx}\right]^2\right\}.$$

Here, x is the direction along the sample chamber, z is the direction along the light beam, n is the refractive index inside the sample chamber, d is the diameter of the sample chamber, and L is the distance between sample chamber and the detector plane. In this equation, [1/n(x)] dn/dx corresponds to the light beam deflection angle, and is small. Its high power in the second term of the equation can be neglected, compared with the first term, then:

$$\frac{\Delta I(x)}{I_0} \simeq \frac{Ld}{n(x)} \frac{d^2n}{dx^2},$$

which shows that the relative changes of the probe beam intensity on the detector plane are proportional to the second derivative of the refractive index inside the capillary. The relationship between the magnitude of the refractive index change and the sample's concentration is approximately linear. Hence, the relative changes of probe beam intensity on the detector plane are also expected to be proportional to the second derivative of the sample's concentration inside the capillary.

Figure 6:
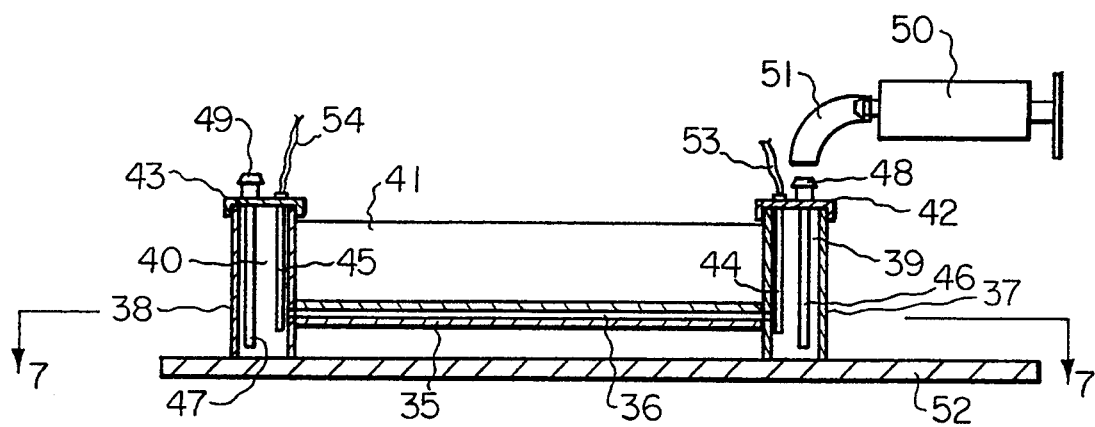
Figure 7:
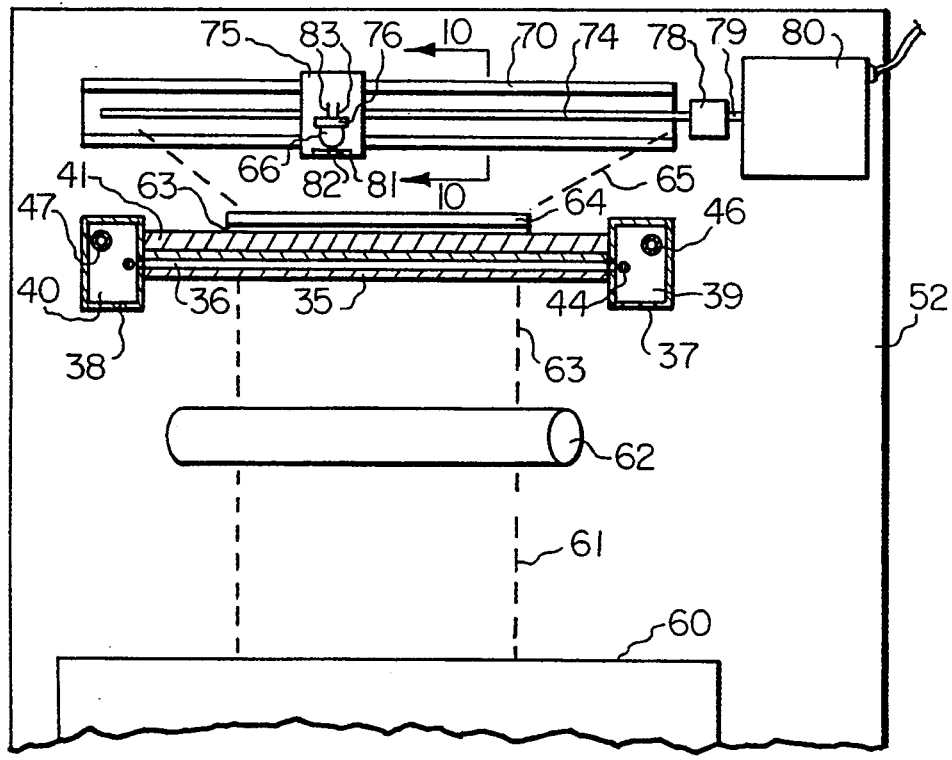

FIGS. 6 and 7 show a capillary electrophoresis apparatus of the invention. As shown, a capillary tube 35, preferably of glass, has a capillary passage 36 therein. Open containers 37 and 38, forming reservoirs 39 and 40, respectively, are secured to the ends of capillary tube 35 so that capillary passage 36 communicates with reservoirs 39 and 40. The assembly is held together as a unit by a member 41 to which the capillary tube 35 and containers 37 and 38 are secured. If the capillary tube is glass, it is preferred that member 41 also be glass and that the capillary be secured thereto by epoxy so that no refractive interface is formed between the two. The containers 37 and 38 may be of any suitable material, such as polyethylene, and secured to member 41 by any suitable adhesive, such as epoxy. Containers 37 and 38 may be provided with tops 42 and 43, respectively, which hold electrodes 44 and 45 in position in reservoirs 39 and 40, respectively. Tubes 46 and 47 extend through tops 42 and 43, respectively, to open near the bottom of reservoirs 39 and 40, respectively. Fittings 48 and 49 on the tops of tubes 46 and 47 where they pass through the respective tops are adapted to receive tubes from a source of, or receptacle for, liquid to be added to, or withdrawn from, the reservoir. Such means may conveniently take the form of a syringe such as shown schematically as 50 with a tube 51 to connect it to the appropriate fitting 48 or 49. The syringe may be manually operated or motor driven, or various other types of pumps or delivery systems could be used. Of course, electrodes 44 and 45 and tubes 46 and 47 could be positioned in the reservoirs by various other means and containers 37 and 38 could remain with open tops. An advantage of providing containers 37 and 38 with tops, and providing that the tops seal such containers, is that the pressure in the containers can then be controlled. Thus, a syringe or other delivery system can be used to pressurize a reservoir to force liquid into the capillary passage, or can be used to draw a partial vacuum in a reservoir to draw liquid from the opposite reservoir into the capillary passage. The unit described may be mounted on a base 52, if desired.

For the unit described, the capillary tube may vary in length as desired, but tube lengths between three centimeters and fifteen centimeters have been found satisfactory for various types of capillary electrophesis. Further, the diameter of the capillary passage may also vary as desired, with diameters of between 10 μm and 100 μm having been found satisfactory. Either round or square capillary passages may be used, but square passages have been found particularly suitable for use with the detector and detection method of the invention. When a square capillary is used, diameter of the capillary refers to the length of a side of the square. The size of the reservoir is not critical, although the volume of a reservoir must be large enough so that the capillary passage can be filled by the particular method being used to fill the capillary. In addition, the electrodes must be in contact with liquid in the reservoir. Thus, the volume of the reservoirs will generally be larger than the volume of the capillary passage extending between them. For example, in the configuration shown in FIGS. 6 and 7, reservoirs each having a volume of about 0.2 milliliters has been found satisfactory for various size capillary passages, such as a fifteen centimeter long passage of 20 μm diameter.

The electrodes 44 and 45 are connected to a source of high voltage (not shown) by wires 53 and 54, respectively. The voltage will preferably be in the range of between 5 KV and 10 KV, depending upon the type of separation being used. Generally, higher voltages will result in faster separation times, but the voltage is limited by the current flow through the sample in the capillary passage which generates heat in the sample. The heat generation must be kept below the level of heat that is readily dissipated through the capillary tube or the capillary tube may explode. The current flow is generally monitored by monitoring current flow in an electrode, generally the current flowing from the cathode. Such monitoring may be with an ampmeter, not shown.

The electrophoresis apparatus shown allows electrophoretic separation using all of the various known electrophoresis separation techniques. These techniques are capillary zone electrophoresis, moving boundary capillary electrophoresis, capillary isotachophoresis, and capillary isoelectric focusing. While with current electrophoresis equipment, separate equipment is needed for each technique, the apparatus described is truly universal in that any of the techniques can be practiced. This is an advantage because in some instances, it may be advantageous to evaluate a sample using two or more of the methods since different methods rely on different properties of the sample. For example, capillary zone electrophoresis and moving boundary capillary electrophoresis separate sample components based on differences in the mobility of each component. Isoelectric focusing separates components based on the different isoelectric point of each component.

Capillary zone electrophoresis generally will require only three steps using the apparatus of the invention. The first is filling the capillary passage with buffer solution. Generally, both reservoirs will be filled with buffer solution. The capillary passage can be filled hydrodynamically by filling one reservoir to a higher level than the other and allowing the buffer from the higher filled reservoir to run into the other reservoir allowing their levels to equalize. Alternatively, if a reservoir is fully enclosed, the reservoir can be pressurized to cause the buffer to flow into the capillary passage. With buffer in both the reservoir and the capillary passage, the buffer is then removed from the anodic reservoir, i.e., the reservoir having the anode or positive electrode therein, and is replaced with sample solution. The high voltage is then turned on and the sample is drawn into the capillary electrokinetically, i.e., by action of the voltage across the capillary passage. The length of the sample plug drawn into the capillary is controlled by the time the sample solution remains in the reservoir and the voltage across the electrodes. When the desired sample plug is introduced into the capillary passage, the sample solution is removed from the reservoir and buffer returned to the reservoir. The voltage remains across the electrodes. Sample separation and movement through the capillary passage continues under the influence of the voltage. After the sample has moved through the passage, the voltage can be disconnected.

Operation in the moving boundary capillary electrophoresis mode is similar. Initially, both reservoirs and the capillary are filled with buffer. In this method, the high voltage can be applied at this point. The buffer is then removed from the anodic reservoir and replaced with sample solution. The sample solution is drawn into the capillary passage electrokinetically. When the desired amount of sample is present in the capillary passage, the sample solution is withdrawn from the reservoir and the buffer again placed in the reservoir. This whole process is easily automated by using two syringe pumps controlled by a computer. Each pump could have its own tube, equivalent to tube 46 shown in FIGS. 6 and 7, extending into the reservoir, or the pumps could be valved through an automatically controlled valve to a single tube in the reservoir.

With capillary isotachophoresis, a first or leading electrolyte is introduced hydrodynamically into the capillary passage. This is followed by hydrodynamic introduction of a sample plug into the capillary passage. This would be achieved by removing the leading electrolyte from the anodic reservoir and filling the reservoir with sample to a higher level than the liquid in the cathodic reservoir. When the desired sample plug flows into the capillary passage, the sample is removed and the second or tailing electrolyte is introduced into the anodic reservoir and into the capillary passage. Thus, the capillary passage includes a sample plug between leading and tailing electrolytes. The high voltage is then connected between the electrodes to perform the separation.

With each of the three separation modes described above, i.e., capillary zone electrophoresis, moving boundary capillary electrophoresis, and capillary isotachophoresis, as the separation takes place, the sample naturally migrates through the capillary passage from the anodic end to the cathodic end.

Figure 8:
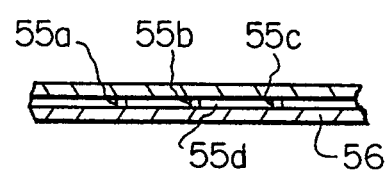

For capillary isoelectric focusing using the described apparatus, the sample, which includes the sample to be separated as well as carrier ampholytes, is introduced into the capillary passage. This may be done hydrodynamically or by placing the sample solution under pressure in one reservoir. After the sample is introduced into the passage, the anodic reservoir is filled with an analyte and the cathodic reservoir filled with a catholyte. The high dc voltage is then connected. Under the influence of the electric field, the ampholytes are arranged by their isoelectric points in order of increasing isoelectric points from anode to cathode. The sample components will migrate to the point in the capillary passage where their isoelectric points are equivalent to the pH established by the ampholytes, to create narrow zones of the sample components. As shown in FIG. 8 components 55a, 55b, 55c are focused into sharp narrow zones in the solute solution 55d within the capillary passage of capillary tube 56. When separation is complete, the separation remains as long as the voltage remains. The separation process can be monitored by monitoring the current flow through the capillary passage. The current flow will reach a minimum and remain stable at that minimum when separation has been achieved. The actual separation will take place usually in about four to seven minutes.

As indicated, the isoelectric focusing separates the sample components into very narrow bands. These narrow bands form very high concentration gradients at their boundaries. Thus, the isoelectric focusing forms very high concentration gradients in the capillary even for low concentrations of sample components. The detection of concentration gradients, rather than detection of concentration, is uniquely applicable to isoelectric focussing and results in high sensitivity of detection and high resolution. The ratio of the sensitivities of detectors based on concentration gradient detection and detectors based on concentration detection may be expressed as a function of the zone or boundary width $\sigma_x$:

$$\frac{(dC/dx)_{max}}{C_{max}} = \frac{1}{\sigma_x \sqrt{\theta}},$$

where $\sigma_x$ is the standard deviation of the concentration distribution in the zone or boundary which is Gaussian. The equation predicts that the sensitivity of a concentration gradient detector increases more quickly with a decreasing zone width than does the sensitivity of detectors based on concentration detection, and that the concentration gradient detector is more suitable than the detectors based on concentration detection for isoelectric focusing which has self-concentration and focusing properties.

If it is desired to mobilize the sample as focused in the capillary passage, the catholyte is withdrawn from the cathodic reservoir and replaced with a solution of different pH. This causes the separated sample to migrate through the passage.

Various concentration gradient detectors can be used with the electrophoresis apparatus described. A single light beam focused through the capillary passage at one end of the passage to measure the deflection of the light beam as the concentration gradients caused by the electrophoretic separation pass through the light beam has been found satisfactory and to have much better resolution than other prior art detectors. This is because the concentration gradient rather than merely concentration is being measured. However, a detector which can measure the separations along the length of the relevant portion of the capillary passage and does not require movement or migration of the separated sample in the capillary passage is preferred for detection when using isoelectric focusing which sets up a stationary separation in the passage since such detector does not require mobilization of the separated sample. By detecting a sample separated by isoelectric focusing without having to mobilize the separated sample, the results are obtained much more quickly. While the focusing itself generally takes between about four and seven minutes, the mobilization usually takes between an additional fifteen to forty-five minutes. By monitoring and detecting the stationary sample, results are obtained as rapidly as the focusing occurs. Further, excellent high resolution is maintained between sample components because this resolution is not lost or distorted through mobilization.

Figure 9:
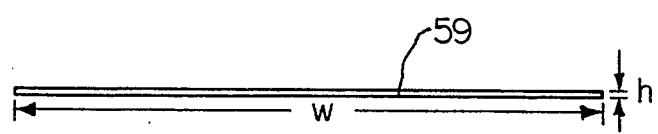

The basic concept of the detectors of the invention is to focus a light beam which comprehends the entire length of interest of the capillary tube in which separations occur onto the capillary tube so that it passes through the sample along the length of the sample containing the separations of interest. This may range from a two cm length along the capillary tube to ten or more centimeters. The intensity of the beam after passing through the sample is sensed or detected in a way that the variations in intensity along the width of the beam which has passed through the desired length of sample is determined. Thus, the width of the beam has to be broken down into many small segments, each individually sensed or detected, in order to provide the desired output. In preferred forms of the invention, a wide but thin light beam 59, FIG. 9 is generated and focused onto the capillary passage so that the width of the beam w will comprehend the length along the capillary passage where separations of interest have taken place, and so that the height of the beam h is preferably smaller than the diameter of the capillary passage. Thus, the height h of the beam shown in FIG. 9 is somewhat exaggerated for purposes of illustration. There are several way such a light beam may be generated including the use of lenses and the use of masks, i.e., an opaque sheet of material with a slit therein. Further, the light for the light beam may originate from a laser, a light emitting diode (LED), a laser diode, or an LED or laser diode array.

Preferred detectors of the invention are shown in FIGS. 7, and 9–12. As shown, a light source 60, such as a laser, or a laser diode, with appropriate lenses as needed, is arranged to direct a light beam 61, of circular cross section, toward capillary passage 36. A cylindrical lens 62 in the path of light beam 61 focuses the circular beam 61 into a thin beam or sheet of light 63 with a width approximately equal to the width of the circular beam. This sheet of light is aligned with and focused onto capillary passage 36. If the width of the beam is shorter than the entire length of the capillary passage, the beam is set to pass through the length of the passage where it is expected that separations of interest will take place. The beam 63 may pass directly through the capillary passage to a detector, or may pass through the capillary passage to lens 64 which expands to the beam 63 before it reaches the detector. The expanded beam is labeled 65. Such expansion can provide increased resolution of detection, particularly where the increments of detection are not as small as desired.

The preferred form of the invention utilizes two alternate detecting or sensing techniques. One is a single detector, such as photodiode 66, mounted to be moved linearly along the width of beam 65 to sense the intensity of light in light beam 65 as a function of the linear position of photodiode 66. Since the light beam being sensed is very thin and the changes in intensity occur in substantially a single direction, i.e., along the width of the beam, accurate alignment of photodiode 66 with the beam from the standpoint of height of the beam is not necessary.

Figure 10:
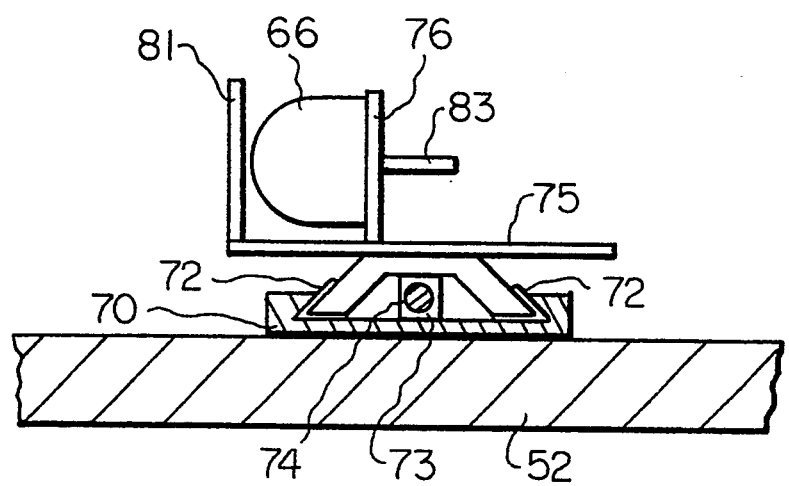

Photodiode 66 may be moved along the width of beam 63 in a variety of ways, and the way movement is obtained is not critical. Any apparatus for moving the photodiode may be used as long as the linear position of the diode can be kept track of. This may merely be a means that once started, will move through the entire length of travel of interest at a constant rate. An example of apparatus for moving diode 66 is shown in FIGS. 7 and 10. A track 70 is mounted on base 52 and receives slidably therein a carriage assembly 71. Carriage assembly 71 includes Teflon ® or similar plastic bearings 72 which ride against track 70 to reduce friction and a threaded member 73 which accepts a threaded shaft 74 therethrough. A platform 75 with bracket 76 and photodiode 66 mounted thereon is secured to carriage 71. Shaft 74, FIG. 7, is coupled through sleeve 78 to the output shaft 79 of stepper motor 80. As threaded shaft 74 is rotated by stepper motor 80, carriage 71, platform 75, and photodiode 66 move along track 70. The direction of travel depends upon the direction of rotation of the stepper motor and the speed of travel depends upon the speed of rotation of the stepper motor. The speed of rotation, direction, and amount of rotation of a stepper motor may be accurately controlled in known manner so the rotation of the motor and travel of photodiode 66 through the width of light beam 65 can be accurately monitored and controlled. During a scan of photodiode 66 along the width of light beam 65, photodiode 66 will produce an output signal proportional to the light intensity of beam 65 striking photodiode 66 and, thus, a signal proportional to the light intensity at all points in the light beam along the path of travel of the photodiode. If it is desired to further limit the width of the segment sensed by photodiode 66, a shield 81 may be mounted in front of photodiode 66 with a slit 82, FIG. 7, therein of desired width. The output of the photodiode is through leads 83. The detector electronics used would be standard and well known.

Figure 11:
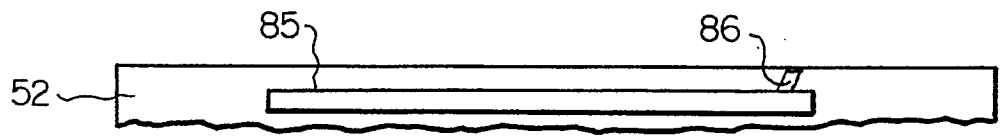

An alternate detector is shown in FIG. 11 and replaces the moving photodiode detector of FIGS. 7 and 10. The detector of FIG. 11 is a photodiode array 85 mounted in the path of light beam 63 after passage through the sample or in the path of expanded light beam 65. Many one dimensional or two dimensional photodiode arrays could be used, with the cost of the array balanced against the desired resolution. The preferred arrays have very small sensing elements spaced along the width of the array. For example, arrays of charge coupled devices which are used in television and video cameras having sensing elements one one-thousandth of an inch in size are readily available, but the larger of such arrays and arrays of a grade with all elements working, are expensive. Arrays with even smaller sensing elements are also becoming available. Such arrays may be obtained with as many as 1024 elements in one dimension. Thus, the width of the array and the width of the light beam comprehended thereby would be broken down into 1024 individually sensed positions. The electronics for scanning an array are standard and well known. The connections between the electroncis and the array are through wires represented schematically as 86.

Figure 12:
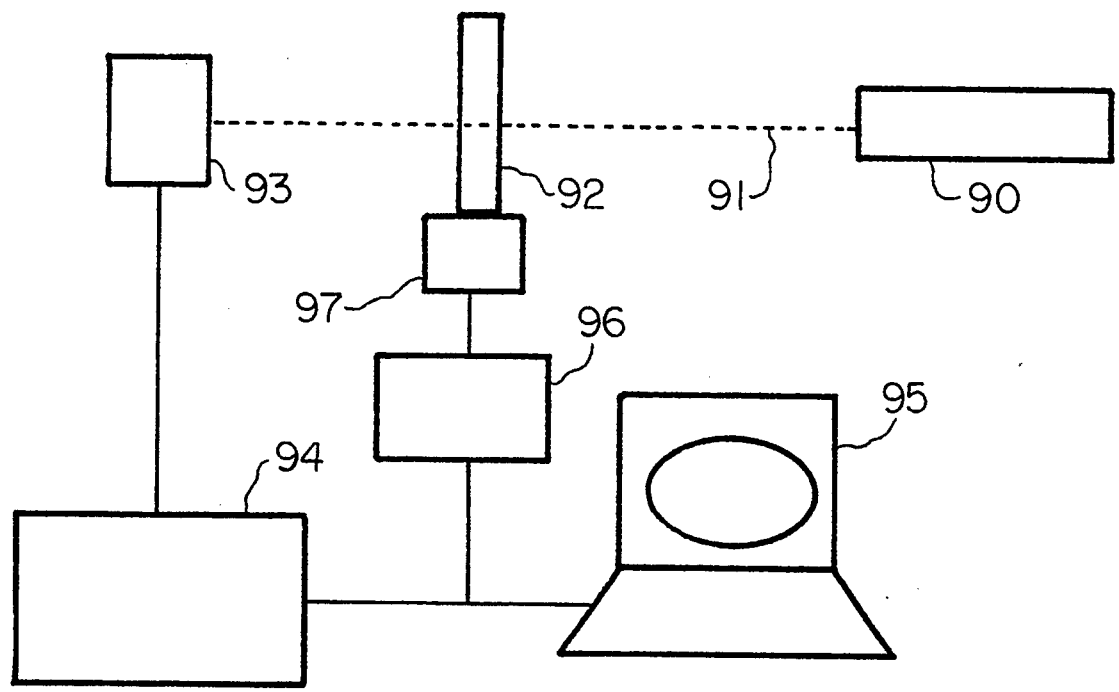

An overall block diagram of a detector system is shown in FIG. 12. The light source is represented by block 90 and includes the necessary components, such as a laser and lenses, to produce the necessary sheet of light, indicated by broken line 91. Light beam 91 passes through the capillary sample chamber 92 to the detector 93 which measures the intensity profile of the beam after passing through the sample. The output of the detector goes to any necessary interface electronics 94 which processes the signals from the detector and sends them to computer 95. Signals from the computer needed to control the detector, such as scanning signals or motor control signals, or other control signals, are sent from computer 95, through interface electronics 94, to detector 93. With such a system, the intensity information obtained can be displayed in real time on the computer monitor and stored in memory for later display or processing. The computer 95 can also operate through interface electronics 96 to operate any reagent pumps, voltage supplies, or other equipment, indicated as block 97, to automate the capillary electrophoresis separations conducted in the capillary sample passage. This can allow coordination between the conditions of the capillary electrophoresis taking place in the sample chamber based upon the detected results.

In a prototype of the detector, a 100 $\mu$m diameter, 6.5 cm long square capillary passage was used in the apparatus shown for the isoelectric focusing. The capillary tube was glass and was glued with epoxy between two glass slides. The capillary passage walls were coated with non-crosslinked acrylamide to eliminate electroosmosis. The containers forming the reservoirs were polyethylene. The apparatus was mounted on a two-axis stage so the tilt angles in the horizontal and vertical planes were adjustable to aid in alignment of the probe light beam with the capillary passage. A He-Ne laser manufactured by Uniphase of San Jose, Calif. was used to generate the probe light beam. The beam from the laser was expanded to a 2 cm diameter beam and was then focused into the capillary passage by a 6 mm focal length cylindrical lens mounted on a three-axis stage. The cylindrical lens produced a sheet of light of about 2 cm in width. After passage through the capillary passage, the 2 cm beam was expanded to a 20 cm beam in the detector plane by a 25 mm focal length lens mounted behind the capillary tube. In this way, 1 cm width in the detector plane corresponded to a 1 mm length of the capillary passage. This makes it easier to measure the intensity profile of the beam. In some experiments, a single photodiode with a shield with 0.1 mm slit therein was mounted on a one-axis stage driven by the moving part of a mode 341B syringe pump made by Orion Research, Inc. of Massachusetts. This was located so the photodiode scanned in the detector plane. The scanning distance of the photodiode so mounted was about 150 mm which corresponded to a 15 mm length of the capillary passage. In other experiments, a one-dimensional, 128 element photodiode array was used to monitor the intensity of the beam in the detector plane. This array was able to monitor a 3 mm length of the capillary passage. The whole system was mounted on a vibration isolation table. The data obtained by the detectors was collected through an IBM DACA board in a PC-AT personal computer, using the ASYST TM software supplied by Asyst Software Technology, Inc., Rochester, N.Y.

In the tests of the systems, all chemicals were reagent grade, and solutions were prepared using deionized water. 10 mM $H_3PO_4$ and 20 mM NaOH were used as the anolyte and catholyte, respectively. NaOH solution was degassed before use, by sparging with helium. Samples used include $\alpha$-chymotrypsin (type II, Sigma), phosphorylase b (Sigma) and ovalbumin (grade V, Sigma). Samples were mixed with ampholyte (pharmalyte pH 3–10, Sigma) solution for a final concentration of 2% ampholyte. Solutions were filtered using 0.2 $\mu$m pore size cellulose acetate filters (Sartorius, Gottingen, Germany). The sample concentration introduced into the capillary ranged from 0.5 mg/mL to 1 mg/mL.

The sample was introduced into the capillary passage by pressure generated by a syringe. A plug of 1% agarose gel in the reservoir of the anodic end of capillary (prepared in the anolyte, 10 mM $H_3PO_4$) was used to avoid hydrodynamic flow in the 100 $\mu$m i.d. capillary. After introduction of the sample into the capillary passage, a 5 KV dc voltage was applied and current passing through the capillary was monitored to follow the focusing process. Typically, the current dropped from 15 $\mu$A to about 2.5 $\mu$A in 4–7 min, and then became stable for hours. This minimum current flow indicates the isoelectric focusing process has been completed.

Figure 13:
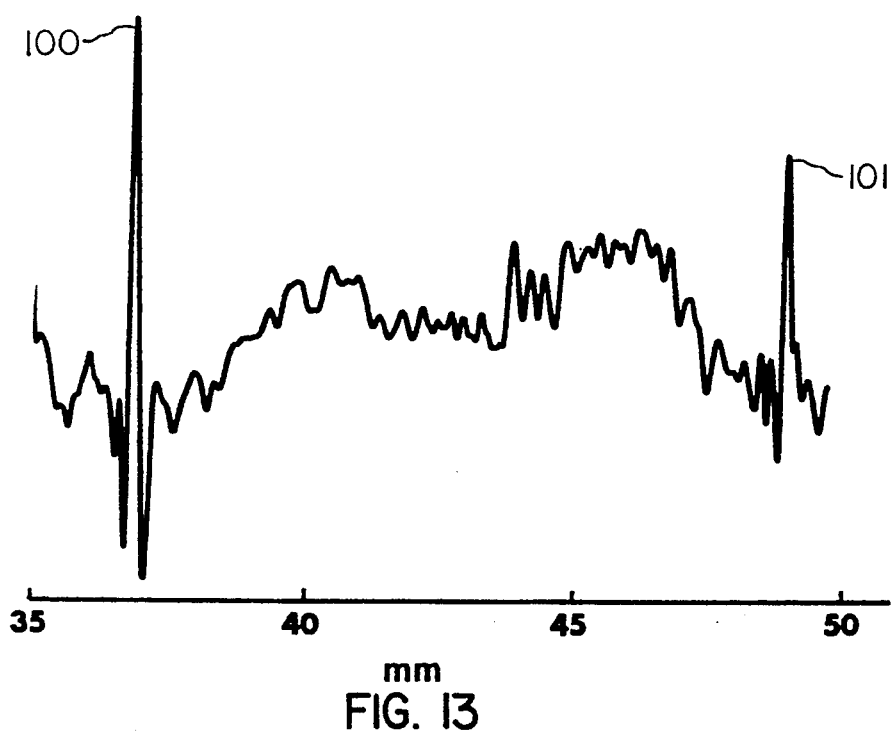
Figure 14:
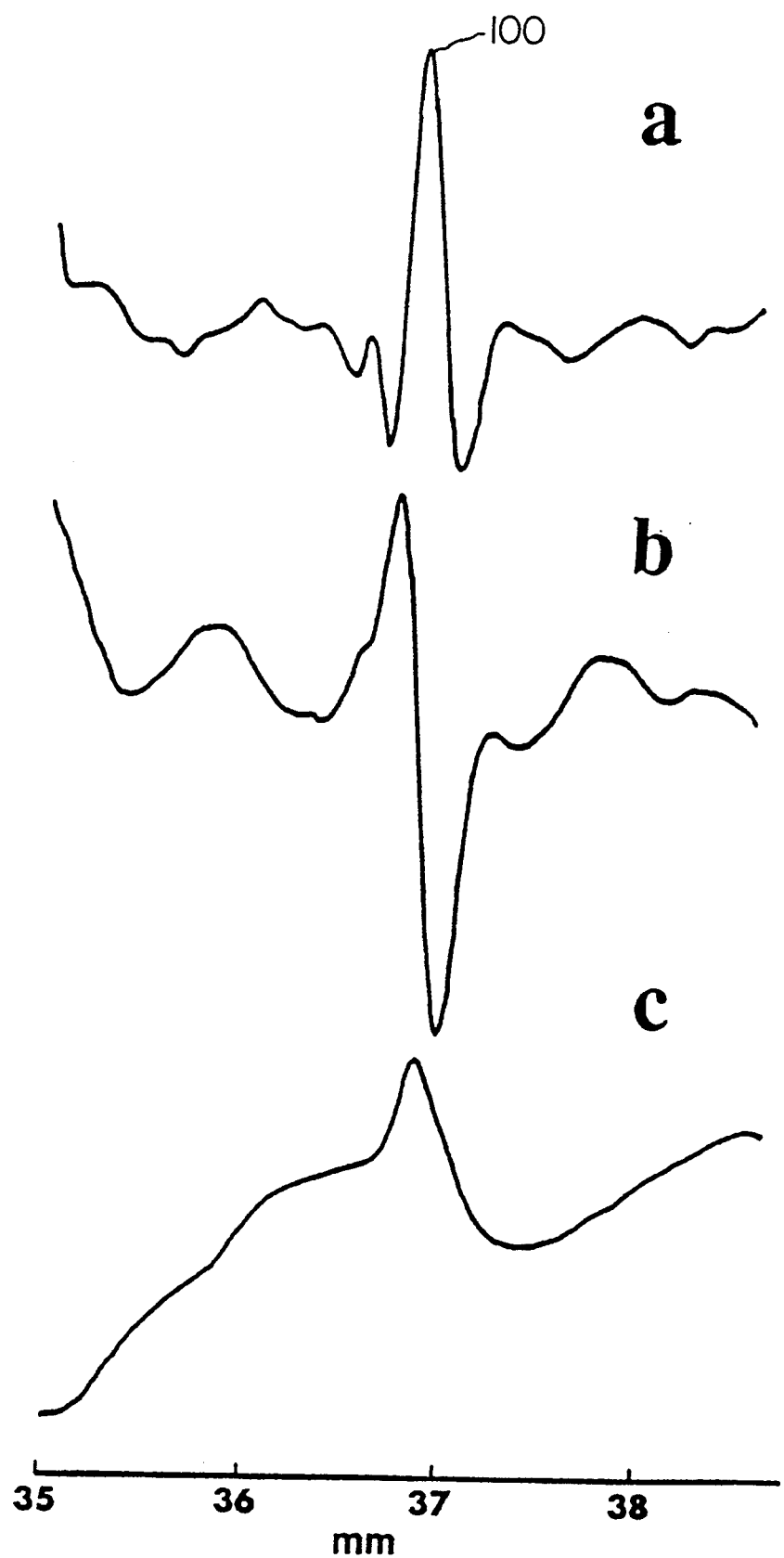

FIG. 13 shows the beam intensity profile detected by the single photodiode scanned across the probe beam which passes through the part of the capillary located 3.5–5 cm distance from the anodic end. Two sharp, high peaks 100 and 101 are observed in the probe beam intensity profile shown in FIG. 13, which correspond to the positions expected for the focused phosphorylase b (isoelectric point 6.3), and ovalbumin (isoelectric point 4.7), respectively. The concentrations of analytes are about 1 mg/mL each. This result demonstrates that the focused proteins inside the capillary can be detected by this simple imaging system. The signal peak 100 corresponding to focused zone of phosphorylase b and its integrals are illustrated in FIG. 14, which clearly shows the second derivative characteristic of the detected signal 100.

Figure 15:
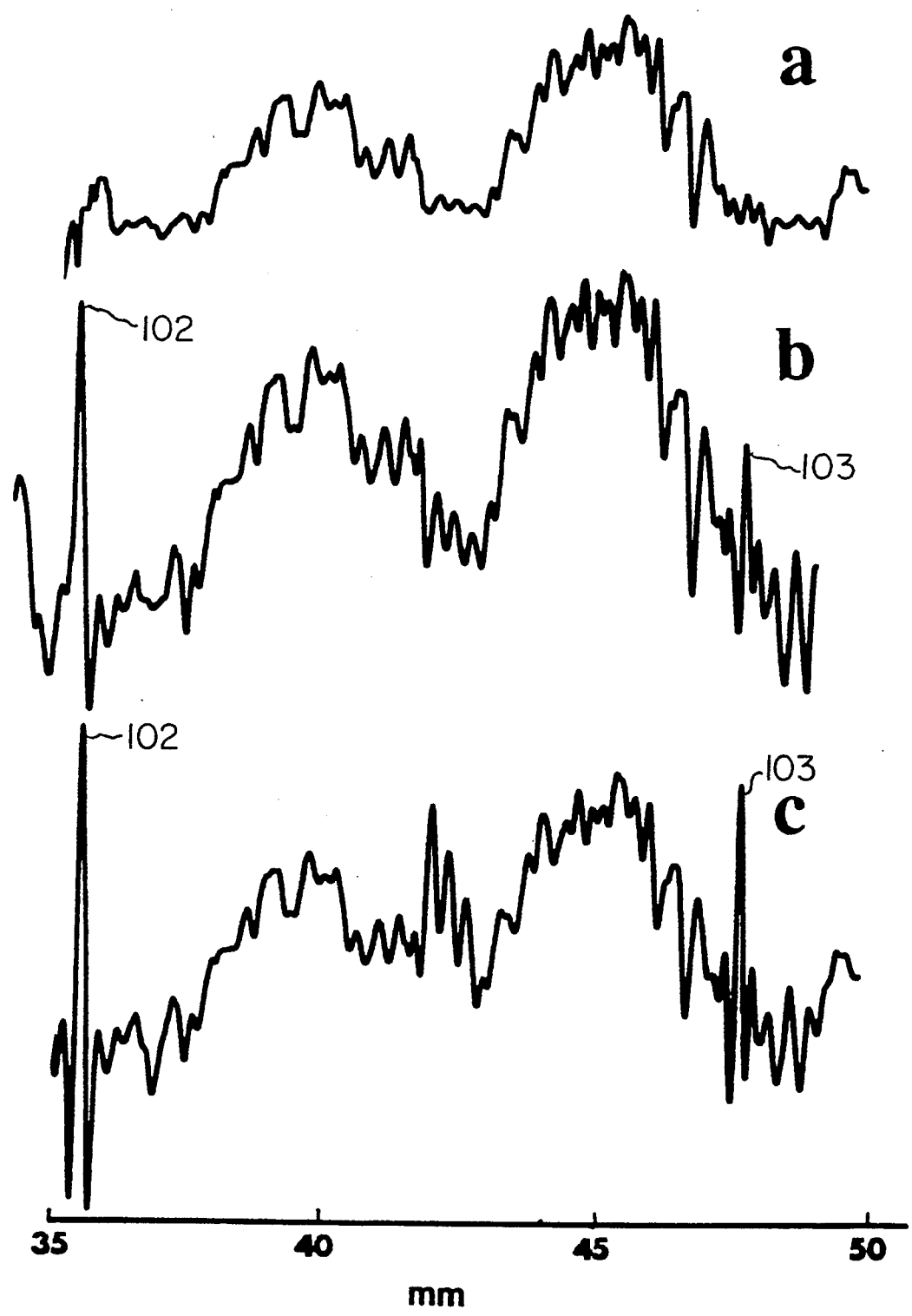

Since this imaging system is an on-line detector, the isoelectric focusing process itself can be monitored. FIG. 15 shows the focusing process of phosphorylase b and ovalbumin. The concentrations of the samples are 0.5 mg/mL, which corresponds to 3.4 pmole of phosphorylase b and 7.2 pmole ovalbumin injected into the 6.5 cm long square capillary. At the beginning (0 Min.) of the focusing, as shown by curve a in FIG. 15, no sharp peaks are observed. The detected signals are the probe beam intensity profile after it passes through the capillary. Many low peaks in FIG. 15 are generated by refractive index defects in the capillary wall or coating materials in the inner wall of the capillary, and their positions do not change with the time, which can be observed in curves a, b, and c of FIG. 15. In curves b and c, two second derivative peaks 102 and 103 appear and become higher with longer focusing time, which correspond to focused phosphorylase b and ovalbumin. In addition to these two high peaks, other small peaks can be observed and become higher with the time in the curves b and c of FIG. 15. Those peaks are associated with the minor components in the samples. It should be mentioned that the concentration gradients generated by the components of carrier ampholytes can also be detected because of the universal nature of the detector. The refractive index fluctuations produced by the carrier ampholytes can be noticed in the integral of the detected signals shown in FIG. 14. However the second derivative nature of the imaging detector effectively reduces the amplitudes of low frequency broad signals generated by the wide bands of the carrier ampholytes. As shown in FIG. 13, high signal peaks can only be observed for high concentration gradients produced at the boundaries of narrow protein zones.

Figure 16:
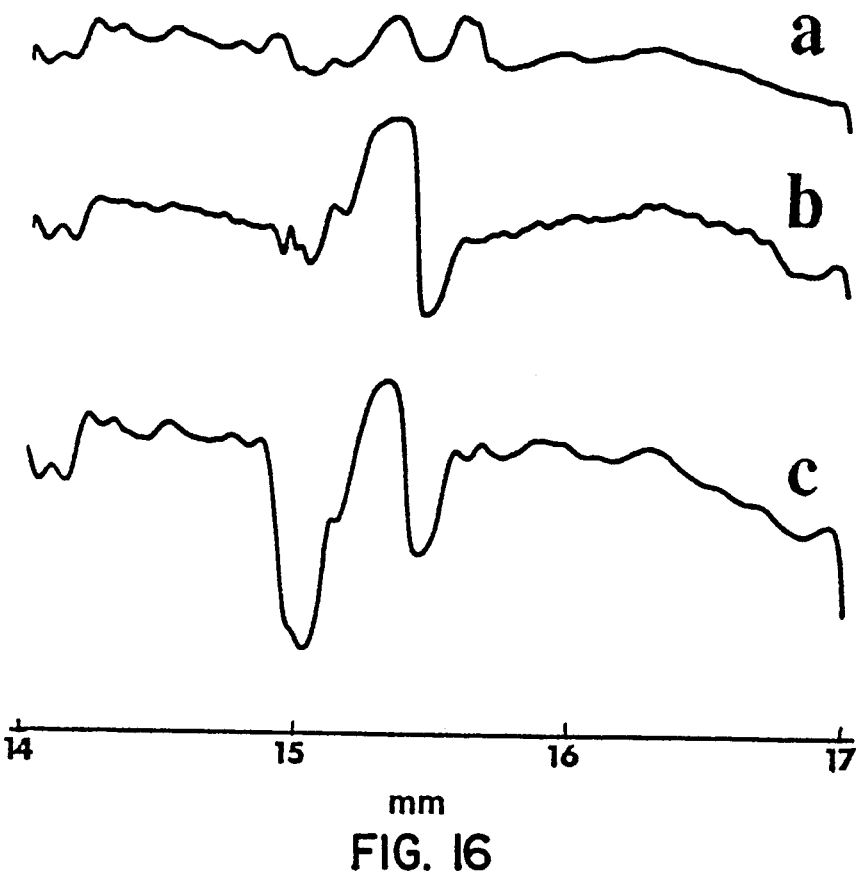

FIGS. 13 and 15 were obtained with the moving single photodiode detector. FIG. 16 shows the focusing process for a $\alpha$-chymotrypsin sample and covers a 3 mm length of the capillary passage. The curves of FIG. 16 were obtained using the 128 element linear photodiode array described above. This clearly shows the practicality of using sensor arrays in the detector of the invention. Further, the results obtained show that the detectors of the invention not only detect the focused analytes in the sample, but can also be used for monitoring and studying the dynamics of the isoelectric focusing process inside the capillary passage.

Figure 17:
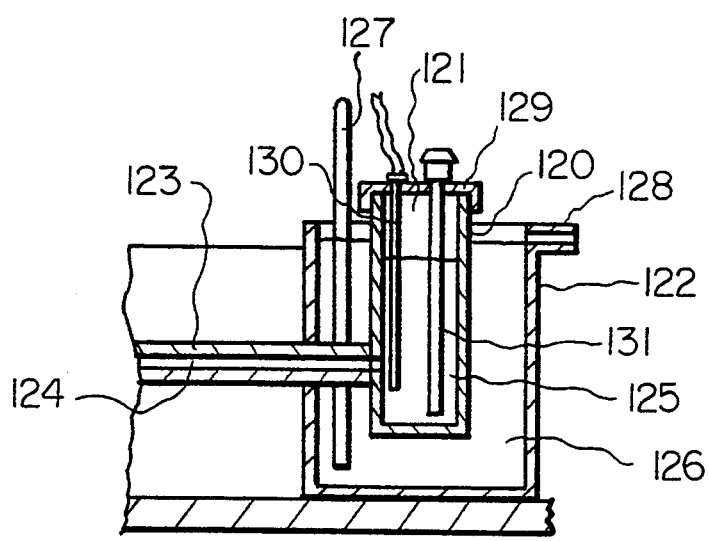

FIG. 17 shows a second embodiment of a sample chamber for the electrophoresis apparatus of the invention. Some sample solutions, such as blood serum samples, contain a high level of salts. This makes the sample have a high degree of electrical conductivity. If such a sample was introduced directly into a capillary passage, the voltage applied for the separation would cause excessive current flow through the sample, excessive heating, and could result in explosion of the capillary tube. Thus, preparation of a sample to remove the salts therefrom is necessary prior to subjecting it to capillary electrophoresis separation. The apparatus shown in FIG. 17 can be used to prepare the sample for electrophoresis as part of the overall procedure.

The modification of the apparatus as shown in FIG. 17 is to provide a container 120 forming the sample reservoir 121 inside a second container 122. Sample container 120 is made of a porous membrane material such as a cellulose acetate membrane material. Alternately, container 120 could be a combination of porous membrane material and other material, such, for example, as a polyethylene container with a porous membrane bottom. Container 122 is made of normal nonporous material such as polyethylene or glass. The capillary tube 123 passes through the wall of container 122 in a sealed manner and is secured in sample container 120 so that capillary passage 124 communicates with sample reservoir 121. Generally, the illustrated construction will be needed for only one of the reservoirs as shown in the apparatus of FIG. 6, usually the anodic reservoir. The sample 125 is introduced into sample reservoir 121, but will not initially flow into capillary tube 124. Water, which may also contain the desired ampholytes, is placed as solution 126 in container 122 so as to surround a portion of container 120. It is preferable to continually flow the water-ampholytes solution through container 122 so for that purpose an inlet tube 127 from a source of water-ampholyte solution may be provided to introduce such solution to container 122 while an outlet 128 may be provided so that solution may flow from container 122. With sample 125 in sample reservoir 121, the salts therein will pass through the porous membrane into the water solution 126 in container 122. Simultaneously, if the water also contains ampholytes, the ampholytes will pass through the membrane into the sample. Thus, the sample can be prepared by the removal of salts and the addition of ampholytes while in the sample reservoir. The sample 125 will remain in sample reservoir 121 for the time required to exchange the salts from the sample to the water through the membrane, and to exchange the ampholytes from the water solution to the sample. When the sample is properly prepared, the sample will be moved into the capillary passage such as through pressurizing the sample reservoir 121. The sample reservoir will include a sealed top 129 to allow pressurization of the reservoir to cause the sample to flow into the capillary passage, the electrode 130, and tube 131, as shown in the apparatus of FIG. 6.

The invention also includes a method of determining the presence or concentration of a particular component that does not have an isoelectric point so would not normally be focused and detected by capillary isoelectric focusing. The method includes the steps of adding a reagent having a well-defined isoelectric point and having a high degree of specificity toward the component to be detected to a sample which may have the component therein, under conditions where the reagent and component will form a combination or complex of the two which will have an isoelectric point different from the isoelectric point of the reagent itself, and then detecting the presence of the complex through isoelectric focusing.

Figure 18:
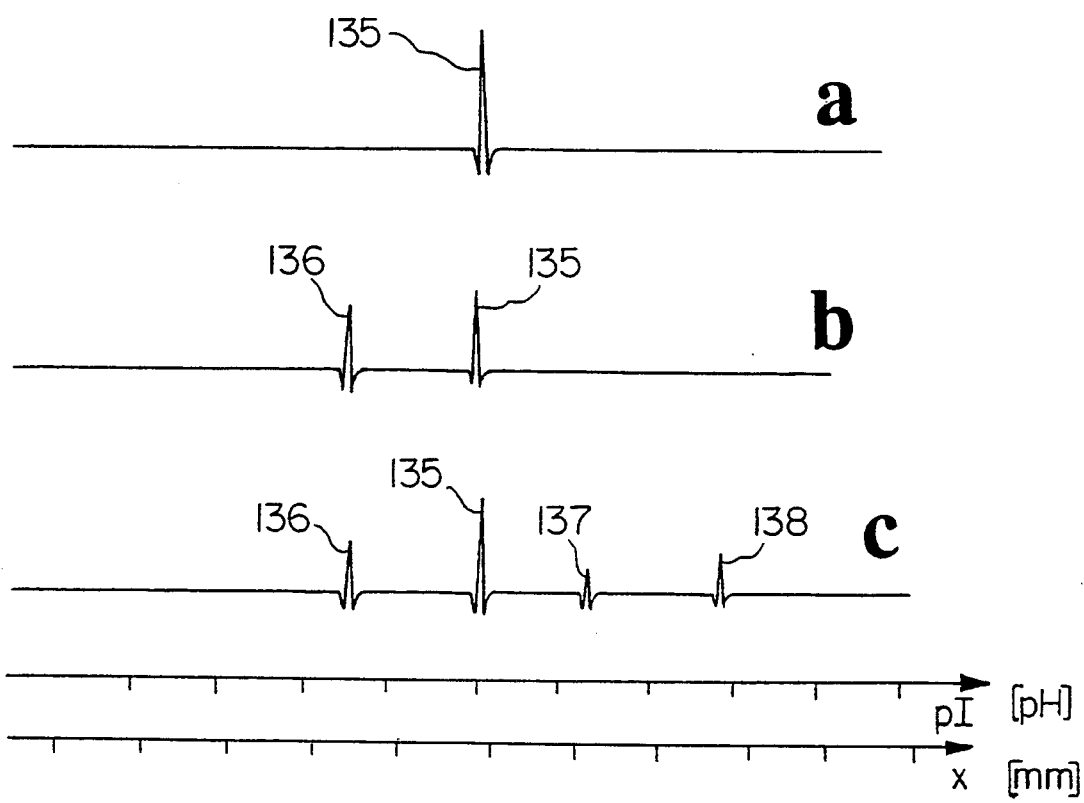

The method is useful in instances where it is desirable to detect the presence of a component, for example a toxin, in a sample, such as a body fluid, but the toxin may not have an isoelectric point so would not normally be separated and detected by isoelectric focusing. In the method of the invention, a reagent having a high degree of specificity toward a target component or analyte is used. The reagent is a substance which has a well-defined isoelectric point and forms a sharp band inside the capillary which may be easily detected through capillary isoelectric focusing and the detectors of the invention as a second derivative of the Gaussian. This is shown by signal 135 in the curves labeled a, b, and c in FIG. 18. The reagent, for example, may be protein which is an antibody for the toxin being looked for or could be a computer designed and laboratory synthesized organic molecule, for example, a synthetic cavity ligand. The component being looked for can be a toxin or other molecule which generally will not have an isoelectric point. The reagent, R, is picked to specifically and strongly interact or react chemically with the target component or analyte A, to form, for example, the product:

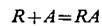

$$R+A=RA$$

The product of the chemical process, RA, has a different isoelectric point and therefore focuses in a different part of the capillary then the reagent R. Thus, the product is indicated as peak 136 in curve b of FIG. 18. In addition, the height of the corresponding signal 136 is proportionally related to the amount of the target component present. The reagent can also be designed to react with several target analytes to produce several different products. In such instance, several corresponding signals 136, 137, and 138 may be obtained as shown in curve c of FIG. 18. It will usually be desirable to ensure that there is an excess of reagent added to the sample so that all of the component present in the sample will react with reagent. In this way, the signal representing the component-reagent product, i.e., peaks 136, 137, or 138, will be proportional to the concentration of component in the sample. The presence of a peak 135 for the reagent as well as a peak for the product will indicate this excess.

Because reagents having very high specificity for components of a sample being looked for can be produced to therefore provide accurate detection and concentration information, the method described using the simple and relatively inexpensive detector of the invention has the potential to replace many tedious analytical procedures and expensive instrumentation.

Figure 19:
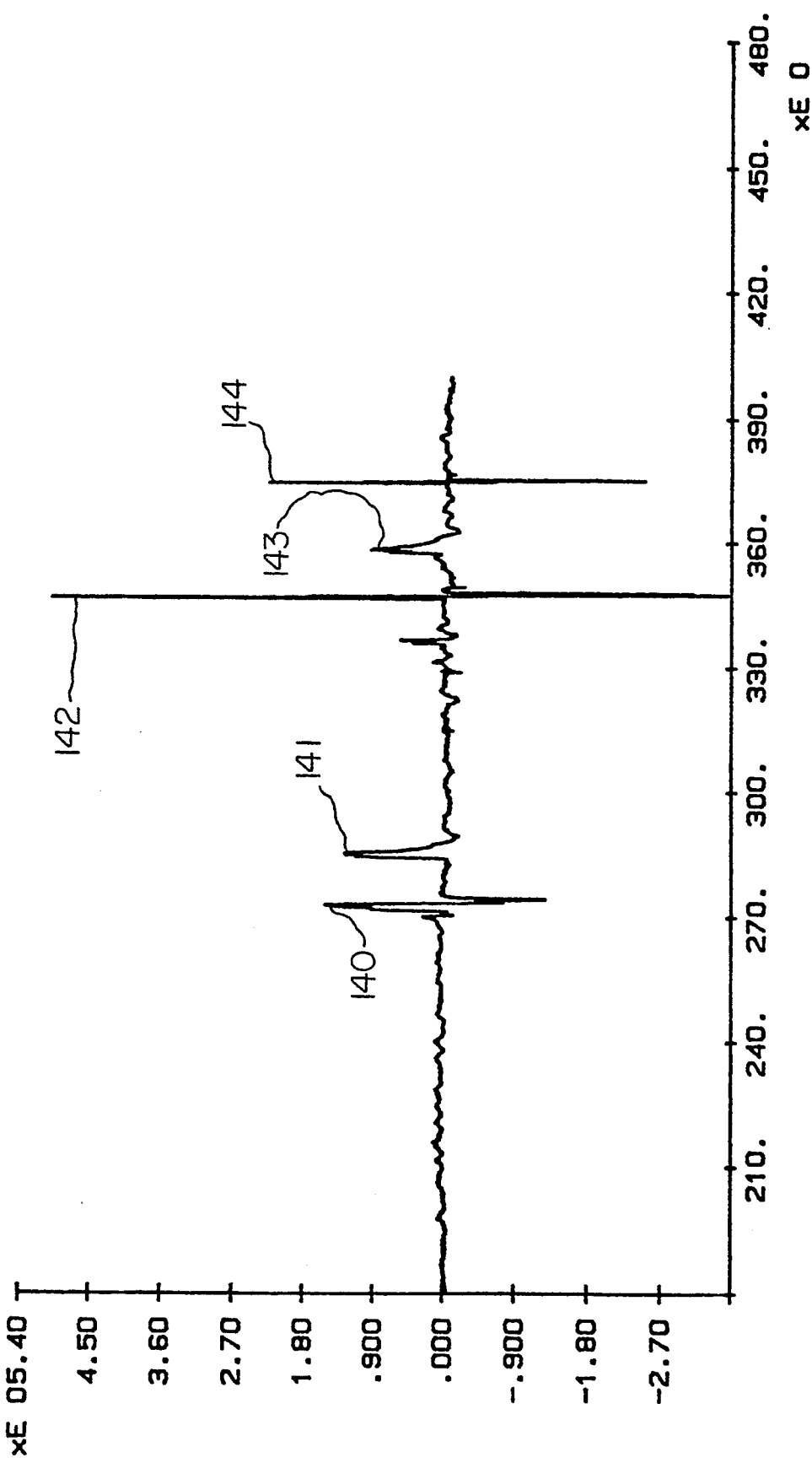

As mentioned previously, the electrophoresis separating apparatus of the invention could be used with a detector similar to those shown in my prior patents having a beam located at one end of the capillary passage and mobilizing the sample separation obtained by isoelectric focusing so that it flows through the capillary and the detector beam. FIG. 19 shows the results obtained using capillary electrophoresis apparatus similar to that shown but with a laser diode as the light source for a light beam passed through one end of a 20 μm capillary passage in a 12 cm long capillary tube. The sample used contained 120 fmol of human hemoglobin indicated by peak 140, myoglobin indicated by peak 141, 270 fmol of human carbonic anhydrase indicated by peak 142, 240 fmol of bovine carbonic anhydrase indicated by peak 143, and 410 fmol of B-lactoglobulin indicated by peak 144. The concentration of the sample was 0.2 mg/mL.

Figure 20:
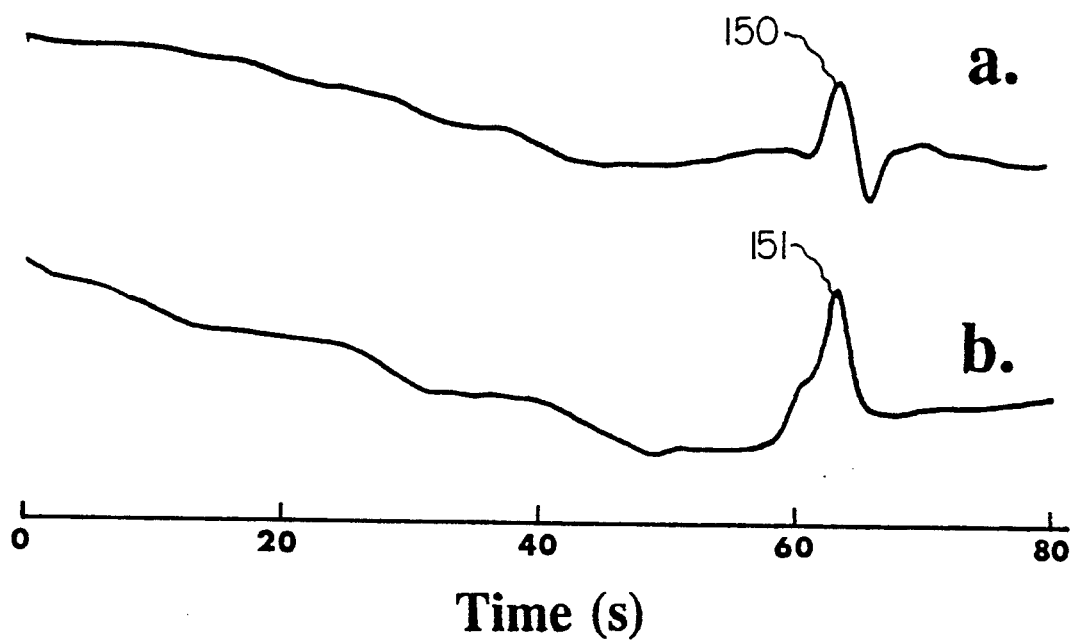
Figure 21:
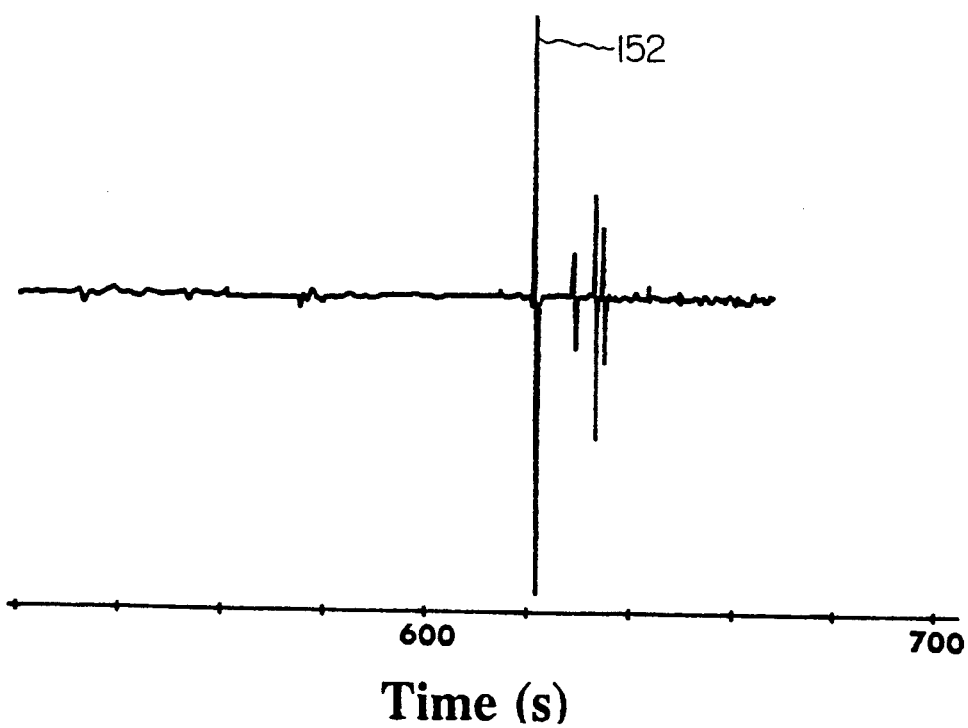

FIGS. 20 and 21 show the difference in separation of a sample by capillary zone electrophoresis, moving boundary capillary electrophoresis, and isoelectric focusing. FIGS. 20 and 21 show electropherograms of ovalbumin separated by the three separation methods. The ovalbumin was purified by the manufacturer with slab zone electrophoresis which is based on a sample's mobility differences. As expected, the electropherogram of capillary zone electrophoresis separation, curve a in FIG. 20, shows only one peak, 150. The electropherogram of moving boundary capillary electrophoresis separation, curve b in FIG. 20, also shows one peak, 151, since it is based on the same separation principal, a difference in component mobility, as capillary zone electrophoresis. However, the electropherogram of the same sample separated by isoelectric focusing, FIG. 21, shows more than four peaks. The highest peak 152, corresponds to ovalbumin, and other peaks can be attributed to impurities or minor components in the sample which have almost the same mobilities as that of ovalbumin, but different isoelectric points from that of ovalbumin. The electropherograms or curves shown were obtained using the apparatus with detector at the end thereof and mobilizing the sample separation obtained by isoelectric focusing. This shows the significant difference and improvement in separation and sensitivity obtained by using isoelectric focusing.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A capillary isoelectric focusing system comprising light transmitting material forming a capillary passage therethrough in which separation of components of a sample take place; means for causing separation of components of a sample to take place in the capillary passage by means of isoelectric focusing and for maintaining such separation in the capillary passage as desired; means for generating a light beam having a width and a height, wherein the width is substantially greater than the height and is sufficient to extend a predetermined length along the capillary passage; means for directing the light beam through the capillary passage so that the light beam passes through a predetermined length of the passage, said predetermined length being such as to simultaneously include any separations of interest due to isoelectric focusing present in the passage; and detector means for detecting the intensity of light in the light beam after passing through the capillary passage at various positions along the predetermined length of the passage and to provide an output representative of the light intensity along the predetermined length of the passage, the intensity of the light at various positions along the predetermined length of the passage being indicative of sample separation along the length of the passage.

2. A capillary isoelectric focusing system according to claim 1, wherein the detector means includes a detector having a narrow sensing area compared to the width of the light beam and means for moving the detector along the predetermined length of the passage.

3. A capillary isoelectric focusing system according to claim 2, wherein the detector is a photodiode.

4. A capillary isoelectric focusing system according to claim 3, wherein a shield is provided between the photodiode and the capillary passage which moves with the photodiode, and an opening in the shield which defines the sensing area of the photodiode.

5. A capillary isoelectric focusing system according to claim 1, wherein the means for generating a light beam is a laser which generates the light beam and a cylindrical lens which shapes the beam.

6. A capillary isoelectric focusing system according to claim 1, including a lens positioned between the capillary passage and the detector to expand the light beam after passage through the capillary passage.

7. A capillary isoelectric focusing system according to claim 1, additionally including a first reservoir and a second reservoir, wherein the light transmitting material is secured to and extends between the first reservoir and the second reservoir whereby the first reservoir, second reservoir, and light transmitting material are secured together as a unit with the capillary passage communicating with and interconnecting the first and second reservoirs and the first and second reservoirs being at opposite ends of the passage, each of said reservoirs being adapted to receive an electrode positioned therein and at least one of said reservoirs adapted to cooperate with a means for adding liquid to or withdrawing liquid from the reservoir.

8. A capillary isoelectric focusing apparatus according to claim 7, additionally including an electrode positioned in each of the reservoirs.

9. A capillary isoelectric focusing apparatus according to claim 8, additionally including means cooperable with one of the reservoirs for adding liquid to or withdrawing liquid from the reservoir.

10. A capillary isoelectric focusing apparatus according to claim 9, wherein the means for adding liquid to or withdrawing liquid from the reservoir is a syringe and a tube secured to the syringe and extending into the reservoir.

11. A capillary isoelectric focusing apparatus according to claim 7, wherein the capillary passage has a diameter of between 10 and 100 microns.

12. A capillary isoelectric focusing apparatus according to claim 7, wherein the capillary passage is 10 centimeters long.

13. A capillary electrophoresis system according to claim 1, wherein the diameter of the capillary passage is between about 10 and 100 microns.

14. A capillary electrophoresis system according to claim 1, wherein the detector means is a light detecting array.

15. A capillary isoelectric focusing system according to claim 14, wherein the light detecting array is a photodiode array.

* * * * *